(12) United States Patent
Puder et al.

(10) Patent No.: US 7,897,591 B2
(45) Date of Patent: Mar. 1, 2011

(54) METHOD OF TREATING FATTY LIVER DISEASE

(75) Inventors: Mark Puder, Medfield, MA (US); Marsha A. Moses, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 11/997,002

(22) PCT Filed: Jul. 28, 2006

(86) PCT No.: PCT/US2006/029517
§ 371 (c)(1),
(2), (4) Date: Jun. 2, 2008

(87) PCT Pub. No.: WO2007/016390
PCT Pub. Date: Feb. 8, 2007

(65) Prior Publication Data
US 2009/0221533 A1   Sep. 3, 2009

Related U.S. Application Data

(60) Provisional application No. 60/703,267, filed on Jul. 28, 2005.

(51) Int. Cl.
*A01N 43/00* (2006.01)
*A61K 37/18* (2006.01)

(52) U.S. Cl. ...................... 514/183; 514/154
(58) Field of Classification Search ............ 514/183
See application file for complete search history.

(56) References Cited

U.S. PATENT DOCUMENTS 3,856,953 A   12/1974   Saltzman

FOREIGN PATENT DOCUMENTS

| WO | 99/61413 A1 | 12/1999 |
|---|---|---|
| WO | WO9961413 * | 12/1999 ............ 49/245 |
| WO | 2004/091603 A1 | 10/2004 |
| WO | 2005/046669 A1 | 5/2005 |

OTHER PUBLICATIONS

Adams et al. (Treatment of non-alcoholic fatty liver disease, Postgrad Med J. May 2006; 82(967): 315-322).*
Wielockx, Ben et al., Nature Medicine, "Inhibition of matrix metalloporteinases blocks lethal hepatitis and apoptosis induced by tumor necrosis factor and allows safe antitumor therapy," 7(11):1202-1208 (2001).
Achord, J.L., The American Journal of Gastroenterology, 88(11):1822-1828 (1993). "Review of Alcoholic Hepatitis and Its Treatment."
Reye, et al., Lancet, 2:749 (1963). "Encephalopathy and Fatty Degeneration of the Viscera."
Schubert, et al., Popper, H. and Schaffner, F. (eds.): Progress in Liver Diseases, Chapter 28, 4th Edition, New York, Grune and Stratton, Inc., pp. 489-510 (1972). "Encephalopathy and Fatty Liver (Reye's Syndrome)."

* cited by examiner

*Primary Examiner*—Sreeni Padmanabhan
*Assistant Examiner*—Timothy E Betton
(74) *Attorney, Agent, or Firm*—Nixon Peabody LLP (57) ABSTRACT

The present invention relates to a method for treating a fatty liver disease or disorder in a patient in need thereof. The method comprises administering at least one matrix metalloproteinase ("MMP") inhibitor to the patient. Fatty liver disease or disorders include, for example, NAFLD, NASH, ALD, fatty liver associated with chronic hepatitis infection, TPN, steroid treatment, tamoxifen treatment, gastrointestinal operations, diabetes and Reye's Syndrome. The method is particularly useful when the fatty liver disease is associated with TPN and the patient is an infant or when the patient is obese. MMP inhibitors useful in the present invention include, for example, Marimastat, tetracyclines, Prinomastat, Batimastat, BAY 12-9566, AG3340, BMS-275291, Neovastat, BB-3644, KB-R7785, TIMP1, TIMP2, doxycycline, minocycline, RS-130,830; CGS 27023A, Solimastat, Ro 32-3555, BMS-272591, and D2163. Marimastat is a preferred MMP inhibitor.

4 Claims, 10 Drawing Sheets

METHOD OF TREATING FATTY LIVER DISEASE

CROSS-REFERENCE TO RELATED APPLICATIONS

This application is a 371 National Stage of International Application No. PCT/US2006/029517 filed on Jul. 28, 2006, which designates the United States, and which claims the benefit under 35 U.S.C. §119(e) of U.S. Provisional Application No. 60/703,267 filed on Jul. 28, 2005, the entire contents of which are incorporated herein by reference.

BACKGROUND OF THE INVENTION

Nonalcoholic fatty liver disease (NAFLD) refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes). In NASH, the fat accumulation is associated with varying degrees of inflammation (hepatitis) and scarring (fibrosis) of the liver.

The term nonalcoholic is used because NAFLD and NASH occur in individuals who do not consume excessive amounts of alcohol. Yet, in many respects, the histological picture of NAFLD is similar to what can be seen in liver disease that is due to excessive intake of alcohol.

The NAFLD spectrum is thought to begin with and progress from its simplest stage, called simple fatty liver (steatosis). That is, fatty liver is the initial abnormality in the spectrum of NAFLD. Simple fatty liver involves just the accumulation of fat in the liver cells with no inflammation or scarring. The fat is actually composed of a particular type of fat (triglyceride) that accumulates within the liver cells. Fatty liver is a harmless (benign) condition.

The next stage and degree of severity in the NAFLD spectrum is NASH. As mentioned, NASH involves the accumulation of fat in the liver cells as well as inflammation of the liver. The inflammatory cells can destroy the liver cells (hepatocellular necrosis). In the terms "steatohepatitis" and "steatonecrosis", steato refers to fatty infiltration, hepatitis refers to inflammation in the liver, and necrosis refers to destroyed liver cells. Strong evidence suggests that NASH, in contrast to simple fatty liver, is not a harmless condition. This means that NASH can ultimately lead to scarring of the liver (fibrosis) and then irreversible, advanced scarring (cirrhosis). Cirrhosis that is caused by NASH is the last and most severe stage in the NAFLD spectrum.

There are many other causes of fat accumulation in the liver besides NAFLD. However, NAFLD and NASH are considered the primary fatty liver diseases. The secondary fatty liver diseases include those that occur in other types of liver disease. Thus, alcoholic liver disease (ALD), discussed below, is the most frequent secondary fatty liver disease. Secondary fatty liver can also occur in chronic viral hepatitis C (HCV), chronic viral hepatitis B (HBV), chronic autoimmune hepatitis (AIH), diabetes and Wilson's disease. (In AIH, the body's immune defense system mistakenly attacks its own liver. In Wilson's disease, an accumulation of copper injures the liver.) In all of these secondary fatty liver diseases, fatty liver is associated with other liver abnormalities distinct from NAFLD and is thought to result from liver cell injury.

Another type of secondary fatty liver disease is unrelated to other specific liver diseases. In these cases, the accumulation of liver fat is due to disturbances in the body's processing (metabolism) of fat (lipid) rather than to direct injury to the liver cells. Such causes include certain drugs (e.g., prednisone), some gastrointestinal disorders such as Intestinal Bacterial Overgrowth (IBO), gastroparesis and irritable bowel (IBS) disorders, patients exposed to chemotherapy in cancer treatments, gastrointestinal operations (bariatric surgery) for obesity, malnutrition, and genetic defects in proteins that process (metabolize) lipids.

The major causes of fatty liver include: (1) protein malnutrition; (2) diabetes mellitus; (3) obesity; (4) corticosteroid treatment; (5) jejunoileal bypass; (6) chronic illnesses associated with impaired nutrition or malabsorption; (7) total parental nutrition (TPN or intravenous hyperalimentation); and (8) pregnancy. (Isselbacher, K. J. and D. K. Podosky, Infiltrative and Metabolic Diseased affecting the Liver in Harrison's Principles of Internal Medicine Eds. Brawnwald, E. et al pp. 1353-54, 1988). Although these causes appear disparate, it has been hypothesized that the accumulation of fat in the liver can be attributed to a perturbation of one of the following steps in the lipid metabolism of hepatocytes and adipocytes: (1) increase free fatty acid delivery to the liver; (2) increased free fatty acid synthesis within the liver; (3) decreased beta-oxidation of fatty acids; and (4) decreased very low-density lipoprotein synthesis or secretion. (Bacon, B. R. et al, Nonalcoholic Steatohepatitis: An Expanded Clinical Entity, Gastroenterology, 107:1103-1109, 1994).

The clinical profile found in patients with fatty liver tend to be similar, but the best descriptions are those associated with alcohol ingestion, thus the name "alcoholic hepatitis." See Achord, J. L., Review of Alcoholic Hepatitis and Its Treatment, The American Journal of Gastroenterology, 88(11): 1822-1828, 1993. Alcoholic hepatitis, also referred to as "florid cirrhosis," "toxic hepatitis" and "acute alcoholic hepatitis," is not a syndrome separate from alcoholic fatty liver. Necrosis is merely another manifestation of hepatic injury related to alcohol. Although on a liver biopsy, much fat can be observed, fat may also be almost totally absent. In addition, liver biopsy may be marked by cell necrosis, polymorphonuclear inflammatory infiltrate of variable intensity and fatty metamorphosis. All of the acute changes induced by alcohol (e.g., fatty liver, alcoholic hepatitis and acute fatty liver with cholestasis) are potentially reversible. The diagnosis can be suspected clinically, but differential diagnosis is best made by needle biopsy of the liver.

The syndrome of encephalopathy and fatty liver was first defined by Reye in 1963 (see Reye, et al, Encephalopathy and fatty degeneration of the viscera. Lancet, 2:749 (1963); Schubert et al, Encephalopathy and Fatty Liver (Reye's Syndrome), in: Popper, H. and Schaffner, F. (eds.): Progress in Liver Diseases. Chap. 28, 4th Edition, New York, Grune and Stratton, Inc., 1972, pp. 489-510). The causes are unknown and may be multiple. Even with today's technological advances, the mortality rate is still very high at 38%.

In view of the above discussion of the enormity of the different fatty liver diseases and disorders, an inexpensive, easy to administer, physically tolerable and effective treatment for this group of diseases is clearly needed.

SUMMARY OF THE INVENTION

The present invention relates to a method for treating a fatty liver disease or disorder in a patient in need thereof. The method comprises administering at least one matrix metalloproteinase ("MMP") inhibitor to the patient.

Fatty liver disease or disorders include, for example, NAFLD, NASH, ALD, fatty liver associated with chronic hepatitis infection, TPN, steroid treatment, tamoxifen treatment, gastrointestinal operations, diabetes and Reye's Syndrome. The method is particularly useful when the fatty liver disease is associated with TPN and the patient is an infant or when the patient is obese.

MMP inhibitors useful in the present invention include, for example, Marimastat, tetracyclines, Prinomastat, Batimastat, BAY 12-9566, AG3340, BMS-275291, Neovastat, BB-3644, KB-R7785, TIMP1, TIMP2, doxycycline, minocycline, RS-130,830; CGS 27023A, Solimastat, Ro 32-3555, BMS-272591, and D2163. Marimastat is a preferred MMP inhibitor.

The present invention further includes the use of a matrix metalloproteinase inhibitor in the manufacture of a medicament for the treatment of a fatty liver disease or disorder. Marimastat is a preferred MMP inhibitor.

DESCRIPTION OF THE INVENTION

The claimed invention is a novel method of treating fatty liver diseases or disorders with a matrix metalloproteinase (MMP) inhibitor. Examples of fatty liver diseases or liver disorders treatable by the present invention include the primary fatty liver diseases NAFLD and NASH and the secondary fatty liver diseases (e.g., ALD, fatty liver associated with chronic hepatitis infection, total parental nutrition (TPN), steroid treatment, tamoxifen, gastrointestinal operations, Reye's Syndrome, gastrointestinal disorders such as Intestinal Bacterial Overgrowth (IBO), gastroparesis and irritable bowel (IBS) disorders, and patients exposed to chemotherapy in cancer treatments). These examples are listed as examples only and the list is not intended to limit the claimed invention to these diseases.

The claimed method of treating fatty liver diseases or disorders includes administering to a patient an effective amount for treating the liver disease of at least one MMP inhibitor. More specifically, the MMP inhibitor used in this invention includes, but is not limited to Marimastat (British Biotech), tetracyclines, Prinomastat, Batimastat, BAY 12-9566 (Bayer), AG3340 (Agouron), BMS-275291 (Bristol-Myers Squibb), and Neovastat (Aeterna labs).

Additional MMP inhibitors useful in the present invention include:

Tissue Inhibitor of Metalloproteinase-1;
Tissue Inhibitor of Metalloproteinase-2;
Tissue Inhibitor of Metalloproteinase-3;
Tissue Inhibitor of Metalloproteinase-4;
Z-Pro-Leu-Gly hydroxamate, minimum 97% (TLC);
4-Aminobenzoyl-Gly-Pro-D-Leu-D-Ala hydroxamic acid, minimum 95% (HPLC);
Actinonin; Dichloromethylenediphosphonic acid disodium salt;
Isoamylphosphonyl-Gly-Pro-Ala dipotassium salt, 95% (HPLC, NMR), Lyophilized powder; N-Methoxysuccinyl-Ala-Ala-Pro-Val-chloromethyl ketone, minimum 95% (HPLC); N-[(2S)-(Methoxycarbonylmethyl)-4-methylpentanoyl]-L-tryptophan-methylamide, >95% (HPLC); Pro-Leu-Gly hydroxamate hydrochloride; and
N-Phospho-Ile(O-ethyl)-Tyr(O-benzyl)-Gly dipotassium salt.

Antibodies, aptamers, antisense nucleic acids and RNAi against MMP may be used. Marimastat™, a broad-spectrum MMP and TNF-X converting enzyme (TACE)—inhibitor is a preferred MMP inhibitor.

The patient is preferably a human but the method may be used to treat any mammal including domestic animals.

This invention is directed to the administration (oral or by any other route) of an MMP inhibitor for the treatment of fatty liver disease or disorders. In yet another preferred embodiment of this invention, the routes of administration can include oral, intramuscular, subcutaneous, transdermal, intravenous or other common routes of administering a drug to a patient.

Alternate routes for patients diagnosed with alcoholic hepatitis or Reye's Syndrome are extremely important as oral administration would not be effective due to the patient's clinical symptoms.

As stated above, the routes of administration can also include oral, intramuscular, subcutaneous, transdermal, intravenous or other common routes of administering a drug to a patient. For example, the pharmaceutical compositions of the MMP inhibitors are formulated so as to be suitable for oral administration. The active ingredient (MMP inhibitor) is contained in a capsule or tablet, preferably in enteric form. The quantity of effective dose supplied by each capsule or tablet is relatively unimportant because the desired total dosage can be reached by administration of either one or a plurality of capsules or tablets or both. The capsules employed may comprise any well known pharmaceutically acceptable material such as gelatin, cellulose derivatives, etc. The tablets may be formulated in accordance with conventional procedures employing solid carriers, lubricants, etc., well known to those skilled in the art. Examples of solid carriers are: starch, sugar, bentonite and other commonly used carriers.

MMP inhibitors useful in the methods of the present invention include, but are not limited to, Batimastat, Marimastat, Prinomastat, the hydroxamates of WO 98/37877 and WO 98/38163, tetracyclines, BB-3644, KB-R7785, TIMP1, TIMP2, adTIMP1 and adTIMP2.

Doxycycline, minocycline, RS-130,830; CGS 27023A, Solimastat, BAY 12-9566, Ro 32-3555, BMS-272591, Ilomastat, D2163 are also MMP inhibitors that are useful in the present invention. For a detailed discussion of MMPs and their inhibitors see Celltransmissions Vol. 17 No. 1 (www.Sigma-aldrich.com/cellsignaling), the disclosure of which is incorporated herein by reference.

As used here, "treating" also includes prevention of a fatty liver disease or disorder in a patient at risk for developing such a disease or disorder.

Dosage of MMP Inhibitors

Dosage levels of MMP inhibitors on the order of about 0.1 mg to about 10,000 mg of the active ingredient compound are useful in the treatment of the above conditions, with preferred levels of about 1.0 mg to about 1,000 mg. A suitable dose may vary widely depending on the condition of the patient. However, a dose of about 0.1 to 300 mg/kg body weight, particularly from about 1 to 100 mg/kg body weight may be appropriate.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

Treatment dosages generally may be titrated to optimize safety and efficacy. Typically, dosage-effect relationships from in vitro initially can provide useful guidance on the proper doses for patient administration. Studies in animal models also generally may be used for guidance regarding effective dosages for treatment of diseases or disorders in accordance with the present invention. In terms of treatment protocols, it should be appreciated that the dosage to be administered will depend on several factors, including the particular agent that is administered, the route administered, the condition of the particular patient, etc. Generally speaking, one will desire to administer an amount of the compound that is effective to achieve a serum level commensurate with the concentrations found to be effective in vitro.

These considerations, as well as effective formulations and administration procedures are well known in the art and are described in standard textbooks.

EXAMPLES

The present invention is further illustrated by the following Examples. These Examples are provided to aid in the understanding of the invention and are not construed as a limitation thereof.

Materials and Methods

Animal Model

Experiments were performed on 5-6 week-old C57BL/6 mice (Jackson Laboratories, Bar Harbor, Me.). The animals, in groups of five, were housed in a barrier room and were acclimated to their environment for at least 72 hours prior to the initiation of each experiment. Animal protocols complied with the NIH Animal Research Advisory Committee guidelines and were approved by the Children's Hospital Boston Animal Care and Use Committee.

Control animals (n=5) received normal chow and water ad libitum. All animals in the experimental groups were fed a fat-free, high carbohydrate liquid diet (HCD) ad libitum placed in one bottle per cage as previously described (3, 62). No additional sources of nutrition or hydration were provided. The HCD liquid solution contained 20% dextrose, a commercial mixture of 2% essential and nonessential amino acids (TrophAmine, B. Braun Medical, Irvine, Calif.), 2 ml trace elements (Trace Elements Injection 4, USP—Pediatric, American Regent Shirley, N.Y.), and 5 ml multivitamins (M.V.I. Pediatric™, Mayne Pharma, Paramus, N.J.). Each liter of HCD contained 30 meq sodium, 20 meq potassium chloride, 15 meq calcium, 10 meq magnesium, and 10 mM phosphate. The bottles were replaced daily with fresh HCD solution. HCD animals (n=5) received HCD only and no additional treatment for 19 days. The HCD+MAR animals (n=15) additionally received 100 mg/kg of Marimastat™ in 0.45% methylcellulose (Sigma-Aldrich Corporation, St. Louis, Mo.) vehicle twice daily via orogastric gavage. The animals were individually weighed every third day and at sacrifice.

Specimen Collection

Mice were anesthetized with 300 µl of 2.5% Avertin (Tribromoethanol, Sigma-Aldrich Corporation, St. Louis, Mo.) by intraperitoneal injection. Approximately 400 µl of blood was collected from each mouse via retro-orbital puncture. The specimens were then placed into serum separator tubes (Becton Dickinson, Franklin Lakes, N.J.), and centrifuged at 4° C. at 8000 rpm for 10 minutes to separate serum. Serum was frozen at −80° C. and delivered to the Clinical Laboratory at Children's Hospital Boston for measurement of aspartate aminotransferase (AST), alanine aminotransferase (ALT), alkaline phosphatase (AP), and total (TB) and direct bilirubin (DB) levels. Furthermore, a fatty acid profile was performed on these samples and TNF-α soluble receptor II levels were determined as described below.

We then performed a midline laparotomy to observe, excise, and weigh the liver. Approximately one half of the liver was fixed in 10% formalin at 4° C. overnight, washed with phosphate buffered saline, and then embedded in paraffin. After cutting 5 µm sections, slides were stained at the Department of Pathology, Children's Hospital Boston with H&E to examine cellular architecture and lipid accumulation, and with periodic acid-Schiff (PAS) to identify the presence of glycogen.

Another portion of the liver was collected as frozen sections, placed in embedding medium (Optimal Cutting Temperature OCT, Sakura Fenetek, Torrance, Calif.), and immersed in cold 2-methylbutane (Aldrich, Milwaukee, Wis.) on dry ice. The samples were stored at −800 C. Sections were stained at the Department of Pathology, Children's Hospital Boston with Oil Red O to detect fat.

Magnetic Resonance Imaging

One section of liver was snap frozen and stored at −80° C. for evaluation by magnetic resonance (MR) spectroscopy to determine the percentage liver fat content (2, 31). MR imaging and spectroscopy were performed on a Bruker 8.5 T magnet. The liver samples were thawed at room temperature 1 hour prior to the MR experiments. Spin-lattice relaxation time T1 measurements were made with the saturation recovery approach using spin echo images with a TE of 6.4 milliseconds and 8 TR's ranging from 0.05-4000 msec. Three 2 mm thick slices were imaged for each sample and the saturation recovery curves were generated from signal intensities measured in identically sized regions of interest within a given slice. Care was taken to exclude macroscopic fat from the selected region of interest. Free induction decays with 1024 time points and a 5 kHz bandwidth were also acquired from each sample using a hard 90 o radiofrequency pulse with 16 signal averages, a 10 s TR, and a flip angle of 90°. Spectra were obtained following Fourier transformation and phasing, and percent fat content was determined relative to water by numerical integration of the areas under the lipid and water peaks by an independent blinded reviewer.

Fatty Acid Analysis

Fatty acid analysis was conducted as described previously (1, 2, 31). Briefly, lipids were extracted from serum and livers, and then fractionated into triglycerides and phospholipids by solid phase chromatography using an aminopropyl column. After appropriate processing, samples were injected into a Hewlett Packard 5890A gas chromatograph for analysis.

ELISA for TNF-α Soluble Receptor II Levels

Circulating mouse TNF-α soluble receptor II levels were determined in serum using a commercial ELISA kit (Quantikine®, R&D systems, Inc., Minneapolis, Minn.). Optical density was read at 450 nm and analyzed with Softmax® PRO Software (Molecular Devices Corporation, Sunnyvale, Calif.).

ELISA for IL-6 Levels

Mouse serum IL-6 levels were determined using a commercial ELISA kit (Quantikine®, R&D systems, Inc., Minneapolis, Minn.). Optical density was read at 450 nm and analyzed with Softmax® PRO Software (Molecular Devices Corporation, Sunnyvale, Calif.).

Western Blot Analysis

Protein extraction was performed according to ActiveMotif nuclear extraction kit protocol (ActiveMotif, Carlsbad, Calif., USA). The lysate obtained was stored at −80° C. for future analysis. Prior to western blot analysis, samples were normalized for protein content using the Bio-Rad Protein Assay (Bio-Rad Laboratories, Hercules, Calif., USA). A standard curve was generated using a range of concentrations of bovine serum albumin (Sigma-Aldrich Corporation, St. Louis, Mo.). The assay was read at 595 nm and analyzed with Softmax® PRO Software (Molecular Devices Corporation, Sunnyvale, Calif.).

30 ug of protein per sample were analyzed by SDS-PAGE. Membranes were then incubated with one of two primary antibodies, a polyclonal rabbit SREBP-1c antibody in a 1:200 concentration (SREBP-1c (K10), sc 367, Santa Cruz Biotechnology, Santa Cruz, Calif., USA), or a monoclonal mouse PPAR-α antibody at a concentration of 5 µg/ml (anti-PPAR-α antibody, MA1-822, Affinity Bioreagents, Golden Colo., USA). The secondary antibodies used were horseradish peroxidase linked donkey anti-rabbit IgG in a 1:5000 dilution (Amersham Biosciences UK limited, Buckinghamshire, UK), or ECL sheep anti-mouse IgG, horseradish peroxidase linked whole antibody in a 1:5000 dilution (Amersham Biosciences UK limited, Buckinghamshire, UK), respectively. Equal protein loading was verified by incubating the same membrane with β-actin antibody in a 1:500 dilution (MS X Actin, Chemicon International, Temecula, Calif., USA). The probed proteins were developed using the Pierce enhanced chemiluminescent substrate for detection of HRP according to manufacturer's instructions (Pierce, Rockford, Ill.).

Immunoprecipitation, SDS-PAGE

Immunoprecipitation was performed according to the Protein-G Immunoprecipitation Kit (Sigma-Aldrich Corporation, St. Louis, Mo.) protocol. Briefly, cell lysate with a total protein content of 1 mg was incubated with 5 µg of anti-PPAR-α antibody (put in which one) overnight at 4° C. with constant mixing. Thirty microliters of Protein-G-agarose beads were then added and the mixture was incubated for an additional 2 hours at 4° C. The beads were then washed with buffer 5 times, with the supernatant being aspirated and discarded. Forty microliters of loading buffer was then added to the beads after the final wash and the mixture was heated to 95° C. in a heating block for 5 minutes. The sample was then centrifuged and the supernatant was analyzed by SDS-PAGE as detailed above.

Statistical Analysis

Comparisons of means between two experimental groups were made using two-tailed, independent t-tests. Comparisons between multiple experimental groups were performed using a one-tailed, ANOVA test. $P<0.05$ was considered statistically significant. All statistical tests were performed using SigmaStat software (SPSS, Chicago, Ill.). Values are listed as mean±standard error of the mean (SEM).

Results

Marimastat™ Ameliorates Macroscopic and Histologic Features of Hepatic Steatosis in C57BL/6 Mice.

All animals survived the protocol. Animals receiving Marimastat™ (HCD+MAR) developed soft stool without gross signs of loss of bowel integrity. No animals had any signs of morbidity. All experimental groups gained weight after 19 days, with an average weight gain of 10% (data not shown). There was no statistically significant difference in animal body weights between experimental groups.

Macroscopic differences in liver appearance between experimental groups were noted at the time of sacrifice. Specifically, livers from the HCD+MAR mice were similar in appearance to those from the chow-fed control group. Conversely, livers from HCD-only mice were pale yellow, suggesting fatty liver changes. There was no significant difference in liver weights between experimental groups (data not shown).

A pathologist blinded to the treatment groups conducted a histological analysis of the livers. Staining with H&E revealed occasional focal cellular infiltrates consistent with focal necrosis in the HCD+MAR group. No acute inflammatory changes were observed in any other group.

Figure 1A:
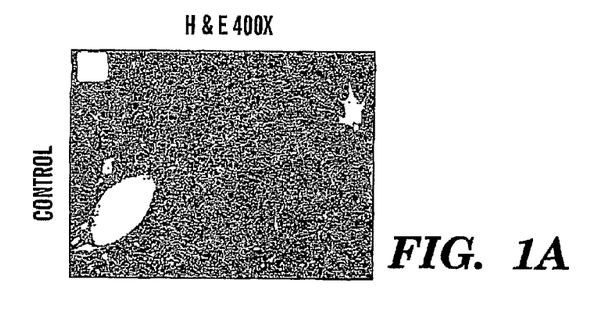
FIGS. 1A-1F show H & E and PAS staining of liver specimens from all experimental groups. Control livers exhibited normal architecture and glycogen storage (1A and 1D), while HCD-only livers revealed extensive microvesicular and macrovesicular steatosis and a very low level of glycogen storage (1B and 1E). HCD+MAR livers were comparable to Control livers in that they showed normal hepatic architecture, and minimal fat (IC and IF). These livers also contained a high level of glycogen storage.
Figure 1B:
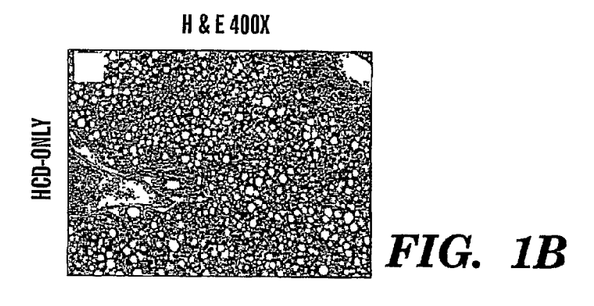
Figure 1C:
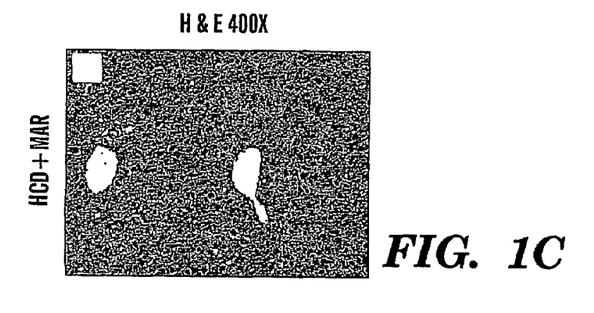
Figure 1D:
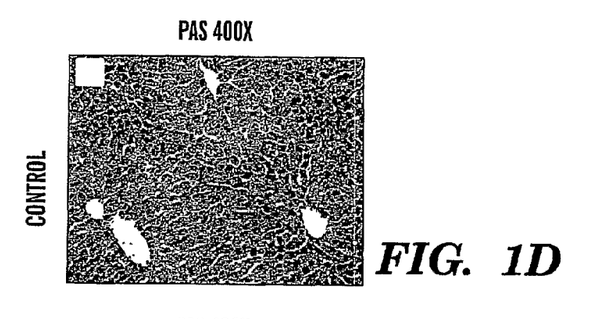
Figure 1E:
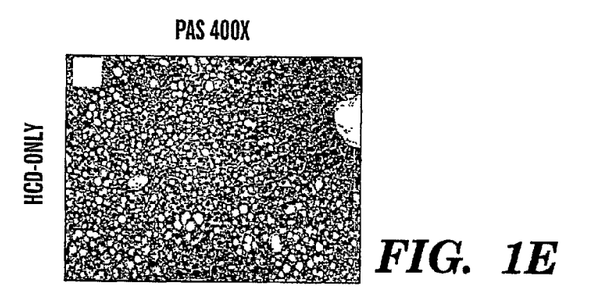

Livers from control, chow-fed mice exhibited typical hepatic architecture (FIG. 1A), and glycogen storage (FIG. 1C). As anticipated, no evidence of hepatic steatosis was noted in this group. In contrast, livers from HCD-only mice showed extensive steatosis, including both macro- and microvesicular types (FIG. 1B). Steatosis was present predominantly in the peri-portal and midzone hepatocytes. The 2-3 cell layers surrounding the central vein were preserved, ending abruptly with an immediate change to steatosis outside its perimeter. HCD-only livers also exhibited low levels of PAS-positive cells, which suggests minimal glycogen storage within hepatocytes (FIG. 1E). The few cells that were PAS-positive in this group were located in the 2-3 cell layer surrounding the central vein that was preserved from steatosis.

Figure 1F:
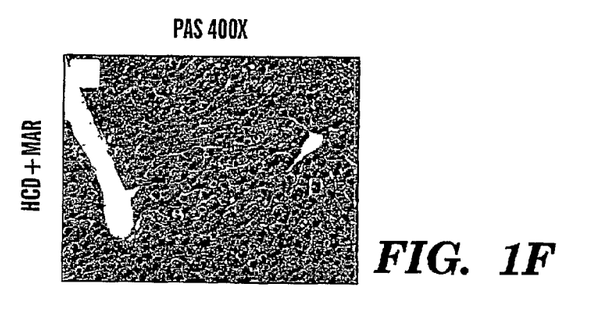

Livers from HCD+MAR mice exhibited fairly normal hepatic architecture, with only rare microvacuoles in the cytoplasm of midzone hepatocytes (FIG. 1C). No definitive steatosis was identified on H&E sections in this group, and PAS staining was highly positive, granular, and widespread (FIG. 1F). Though PAS staining was diffuse, it was most prevalent around the portal and central veins, and less prominent in the midzone.

Figure 2A:
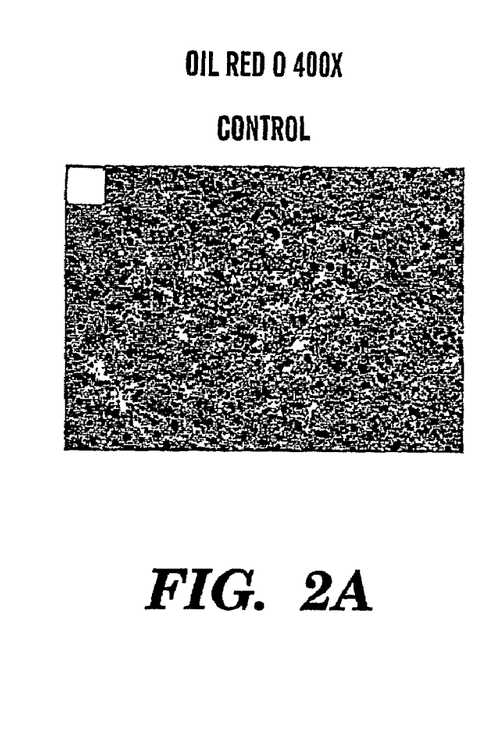
FIGS. 2A-2C illustrate that staining with Oil Red O showed the presence of lipid droplets in HCD-only livers, which was not present in Control or HCD+MAR groups.
Figure 2B:
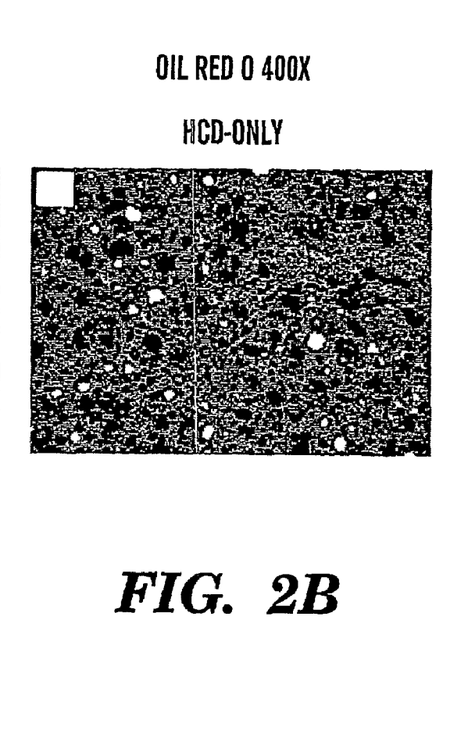
Figure 2C:
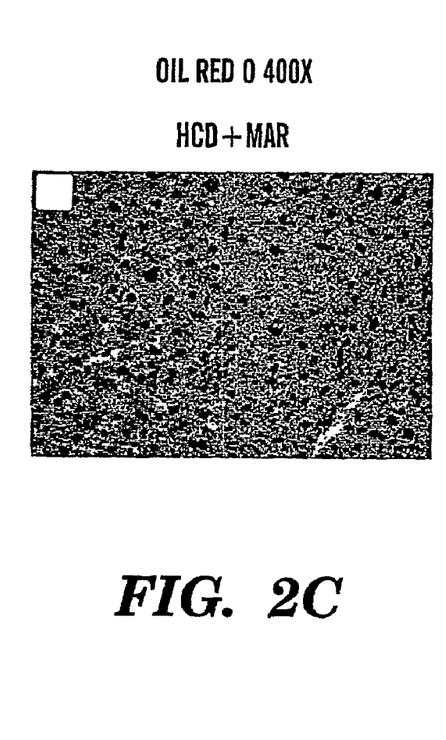
Figure 3A:
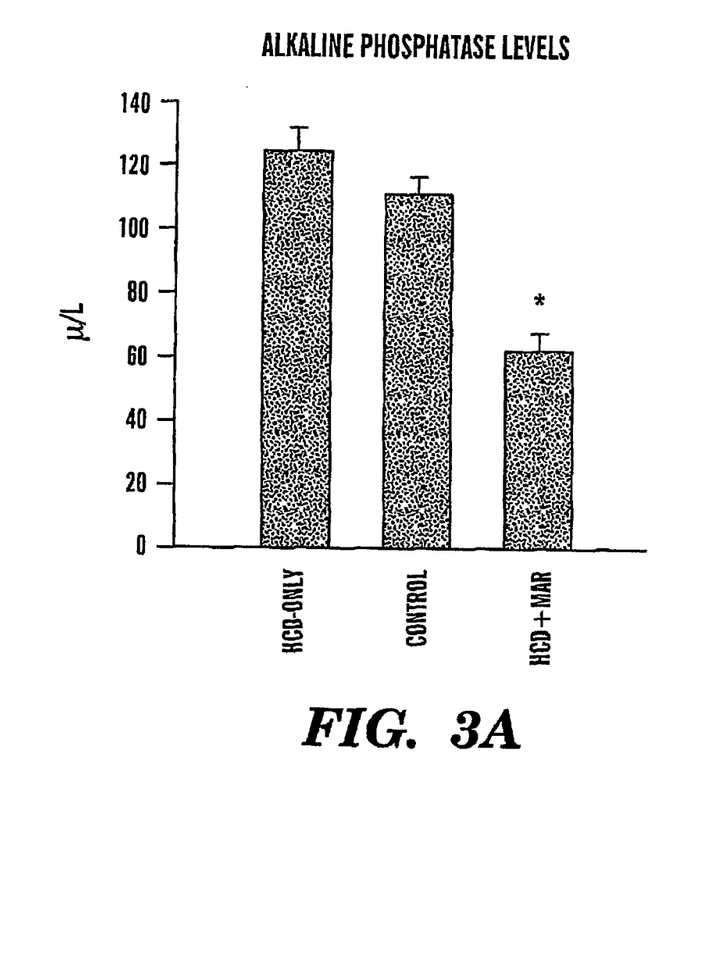
FIGS. 3A-3D show liver enzyme and bilirubin levels. A. Alkaline phosphatase (AP) B. Alanine amino transferase (ALT) C. Total bilirubin (TB) D. Direct bilirubin (DB). AP levels were significantly lower only in the HCD+MAR group ($P<0.001$) (FIG. 3A). ALT (a specific marker for liver injury) levels were significantly elevated in the HCD-only group compared to control ($P<0.03$) and lower in the HCD+MAR group ($P<0.001$) (FIG. 3B). Total and direct bilirubin levels again were significantly lower in the HCD+MAR group compared to HCD-only group (FIGS. 3C, D). More striking, the DB levels were 0 in all 15 mice in the HCD+MAR group ($P<0.001$).
Figure 3B:
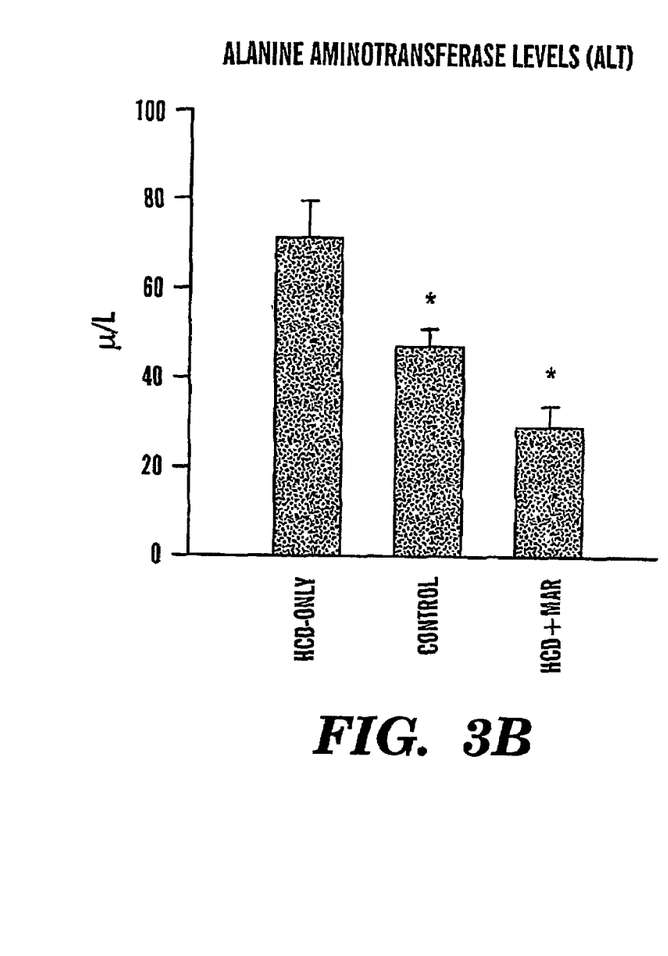
Figure 3C:
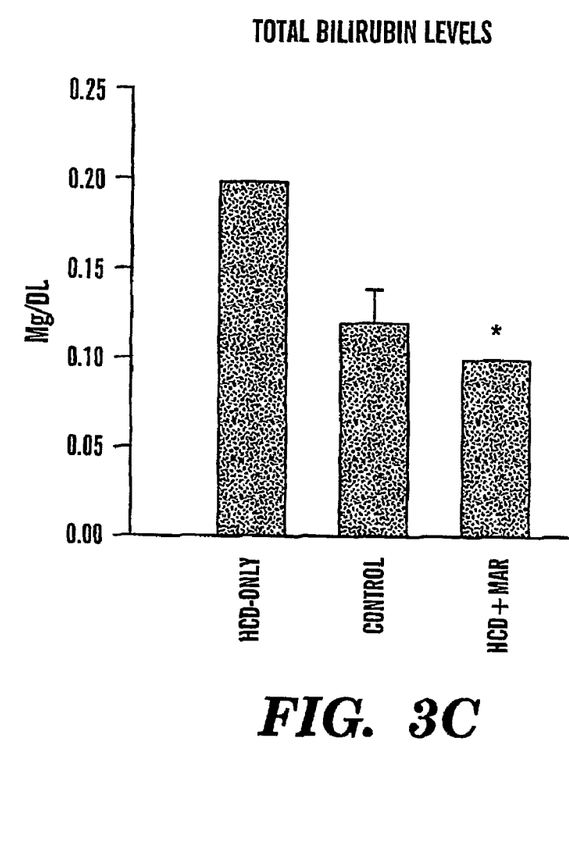
Figure 3D:
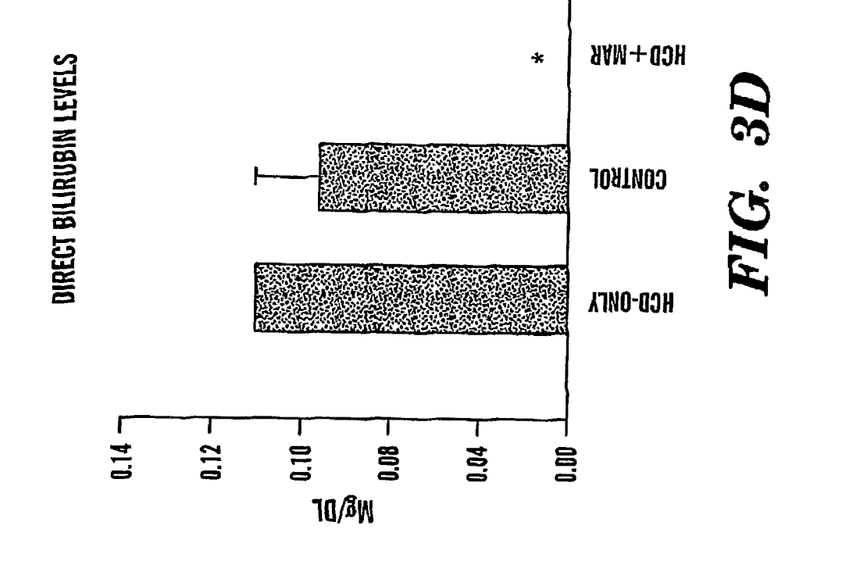

Oil Red O staining revealed minimal fat in control livers (FIG. 2A). Livers from BCD-only mice exhibited diffuse presence of fat throughout the liver parenchyma (FIG. 2B), whereas livers from HCD-MAR mice showed minimal presence of fat (FIG. 2C), consistent with levels observed in the control group.

Marimastat™ Ameliorates Hepatic Steatosis in C57BL/6 Mice Determined by MR Spectroscopy.

MR spectroscopy was used to quantify hepatic fat content. Baseline fat content was established using livers from control, chow-fed mice. A close correlation was observed between the percent fat calculated from the MR spectroscopy and the degree of T1 shortening determined from the T1 relaxation curves (data not shown).

Control, chow-fed animals were found to have a liver fat content of 3.4±0.6%. In contrast HCD-only mice exhibited a significant increase in liver fat content with a value of 24.1 ±1.7%, $P<0.001$. Concomitant treatment with Marimastat™ (HCD+MAR) resulted in a significant decrease in liver fat content relative to HCD-only mice (8.1±1.2, $P<0.05$). The HCD+MAR and control, chow-fed animals showed no significant difference in liver fat content.

Marimastat™ Improves Serum Liver Function Tests in Hepatic Steatosis in C57BL/6 Mice.

To detect the presence of liver injury, liver function tests were conducted on all experimental groups. HCD-only animals exhibited significantly higher values than HCD+MAR animals on all tests (FIG. 3, $P<0.05$), with the exception of aspartate aminotransferase (data not shown). This suggests that the biochemical damage induced by HCD involves both liver parenchyma and bile ducts and that treatment with Marimastat™ can abrogate this damage. When comparing chow-fed control animals to HCD-only animals, similar results were observed, with the exception that alkaline phosphatase and direct bilirubin were not significantly different. The lowest levels for all hepatic function tests were in the HCD+MAR group.

Marimastat™ Does not Prevent Essential Fatty Acid Deficiency in C57BL/6 Mice.

A high carbohydrate, low fat diet stimulates hepatic lipogenesis (2, 31). Essential fatty acid deficiency (Mead acid: Arachidonic acid ratio (M:A)>0.2 in the serum lipid) fosters hepatic steatosis (31, 32, 61) principally through the process of de novo lipogenesis. In our model, maximum steatosis is achieved through the administration of a high carbohydrate, fat-free diet. These animals are indeed essential fatty acid deficient as determined by a M:A of 0.43±0.06 in the serum. In contrast, animals receiving normal chow have a normal fatty acid status, with a M:A of 0.03±0.01. The M:A of HCD+MAR, however, is 0.47±0.08, confirming essential fatty acid deficiency in both HCD groups.

Marimastat™ Decreases Serum TNF-α Receptor II Levels.

In an attempt to characterize the intensity of inflammatory events occurring during HCD-induced liver injury, TNF-α-soluble receptor II (TNFRII) levels were measured as described. The levels of TNFRII in HCD-only animals were significantly higher (599±61) than those of HCD+MAR animals (468±34, $P<0.05$), but this would represent a small difference clinically. There was no statistically significant difference when comparing circulating TNFRII levels to control animals (538±48).

Marimastat™ Increases Serum IL-6 Levels.

Figure 4:
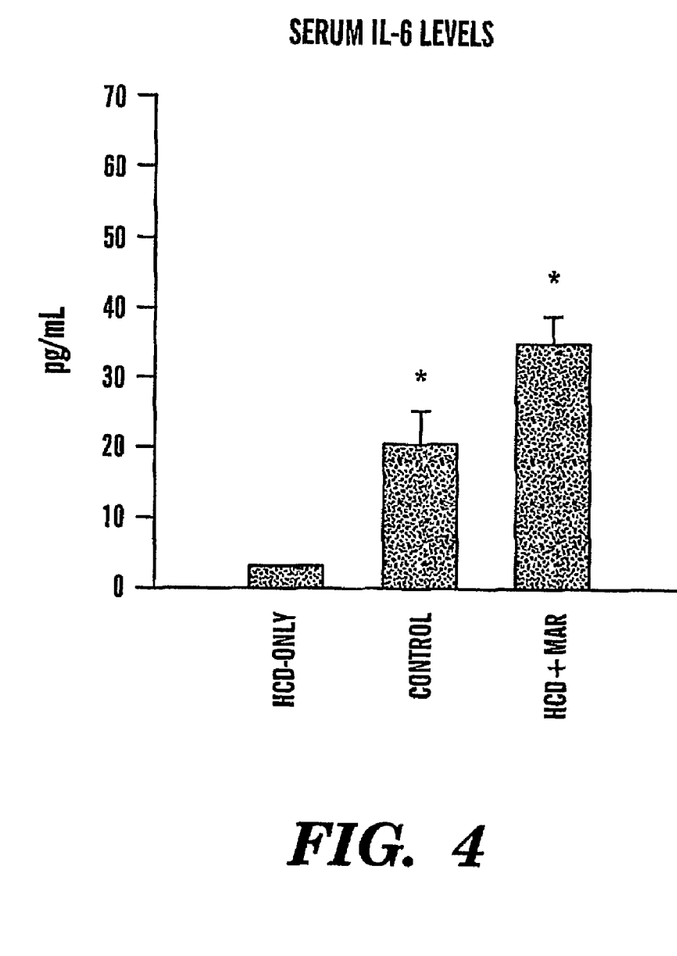
FIG. 4 shows serum IL-6 levels as measured by ELISA. Significant elevations in IL-6 levels were observed in the HCD+MAR group as compared to the HCD-only group ($p=0.001$). HCD-Only IL-6 levels were also significantly lower than the control group ($p=0.008$).

Serum IL-6 levels were measured as described to determine whether this cytokine is involved in the clearance of fat from the liver by Marimastat™. Both the HCD+MAR and the chow-fed control groups had significantly higher levels of IL-6 than the HCD-only group ($P=0.001$, $P=0.008$), while no significant difference was observed between the HCD+MAR and chow-fed controls (FIG. 4).

Marimastat™ Increases PPAR-α but not SREBP-1c Levels.

Figure 5A:
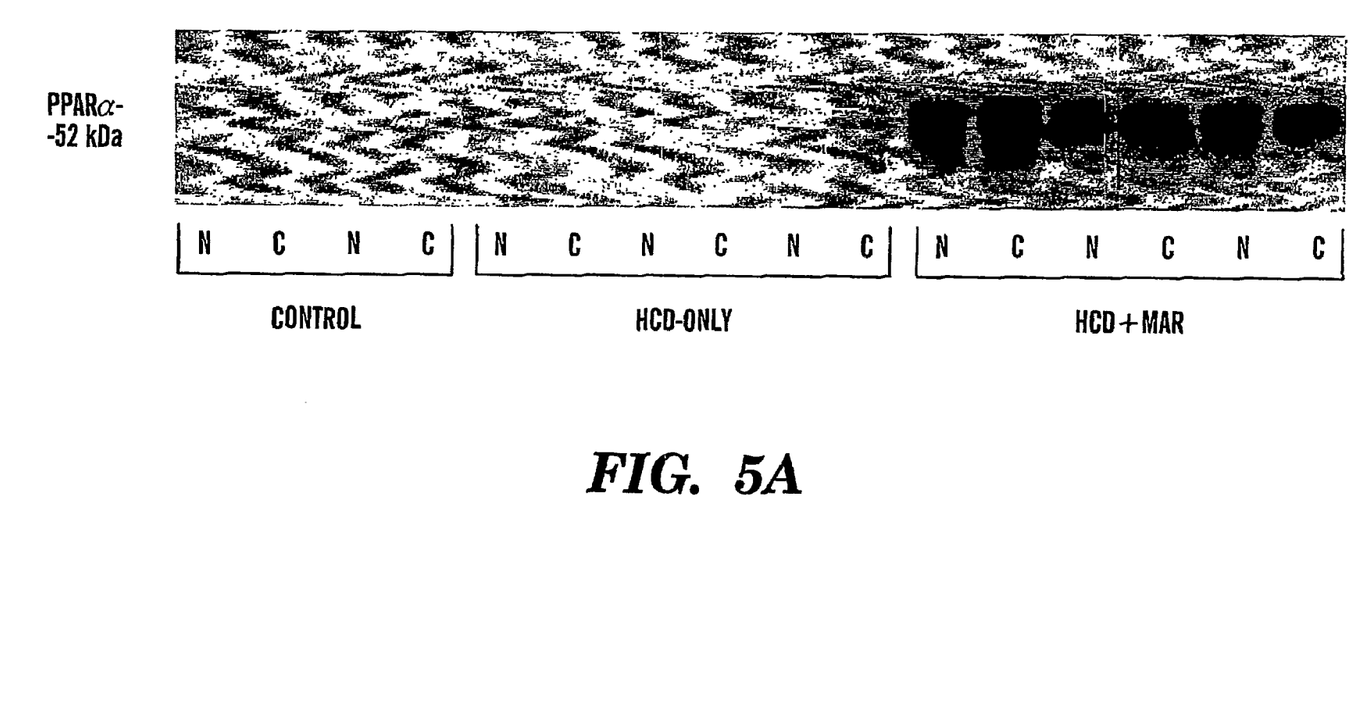
FIGS. 5A-5C show protein expression analysis of PPAR-α in Control, HCD-only, and HCD+MAR groups. A. Western blot (SDS-PAGE) analysis of control and treatment groups with cytosolic and nuclear fractions, with increased expression in the HCD+MAR group. B. Densitometric interpretation of the Western blot showing a significant increase of PPAR-α in the HCD+MAR group. C. Western blot (SDS-PAGE) analysis following immunoprecipitation showing increased phosphorylation of PPAR-α in the HCD+MAR group.
Figure 5B:
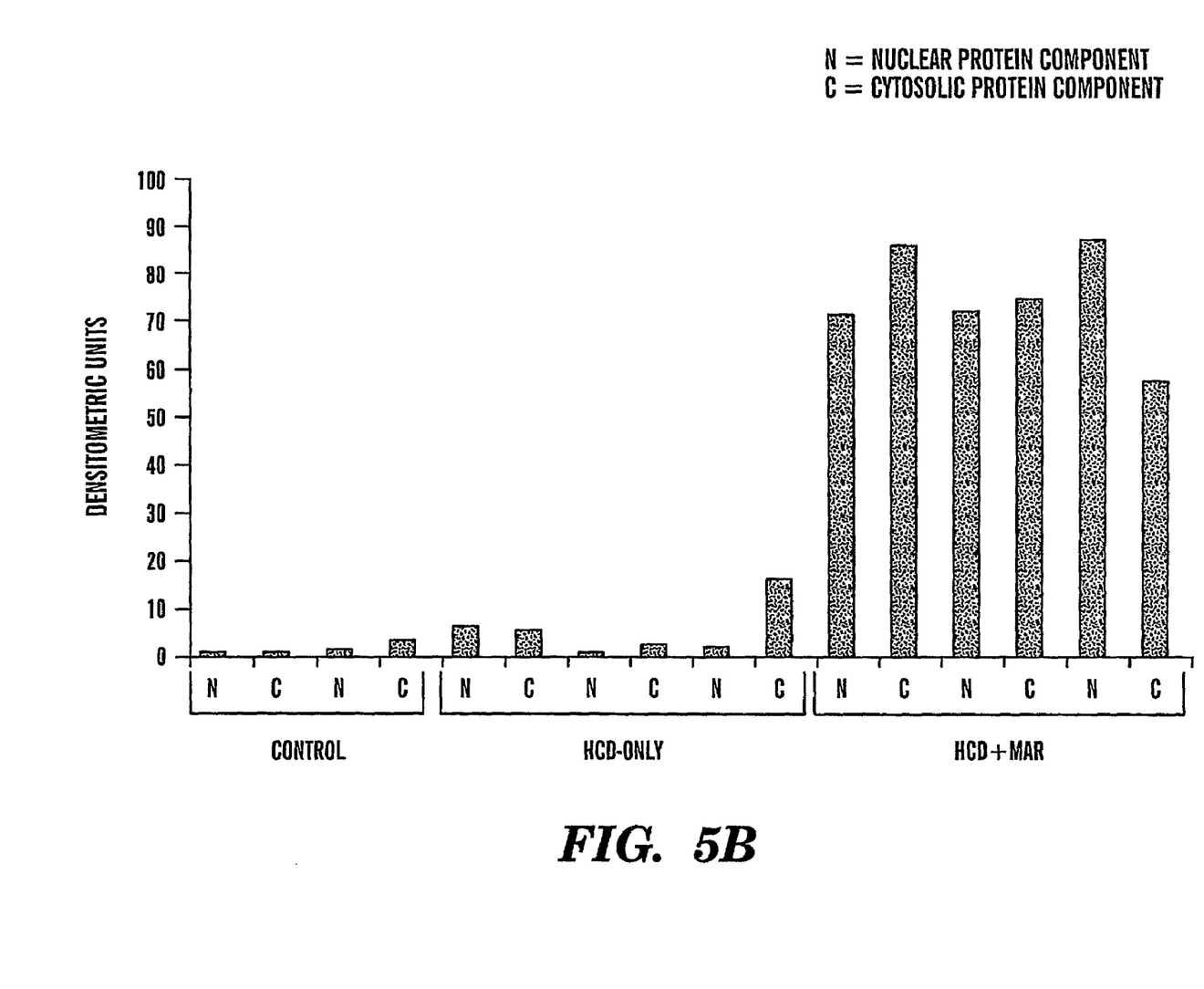

Animals in the HCD+MAR group were found to have higher (151.7±3.4) levels of PPAR-α than animals in both the HCD-only group (11.5±4.4, $P<0.02$) and the control group (3.3±1.7), as measured by Western blot densitometry (FIGS. 5A, 5B). No significant difference was observed between the nuclear and cytosolic protein components in densitometric analysis. The two values for each animal were summed, and then subjected to statistical analysis. SREBP-1c protein levels were unchanged across the treatment groups.

Marimastat™ Increases Phosphorylation of PPAR-α.

Figure 5C:
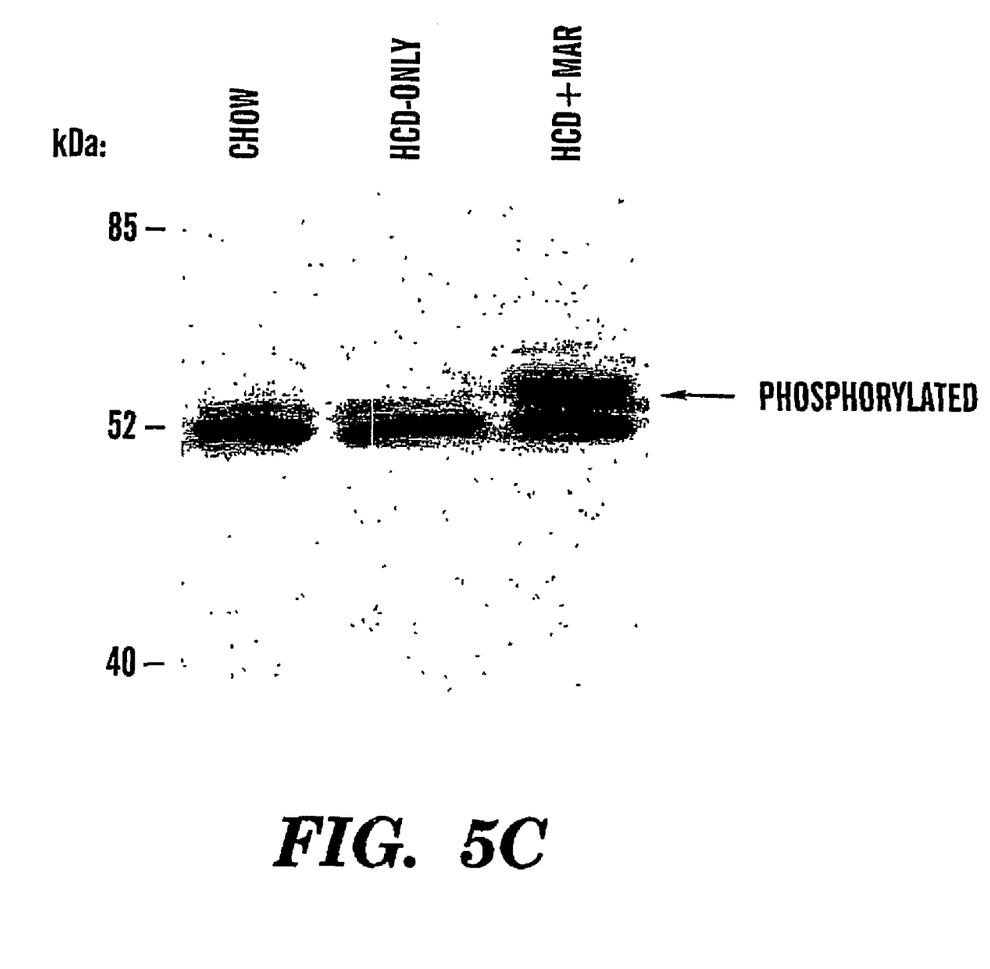

Immunoprecipitation followed by SDS-PAGE analysis revealed that PPAR-α in the control and HCD-only groups exists primarily in the unphosphorylated form. In contrast, the HCD+MAR group showed a marked increase in phosphorylation (FIG. 5C).

Marimastat™ Improves Hepatic Secretion of Fat.

Figure 6A:
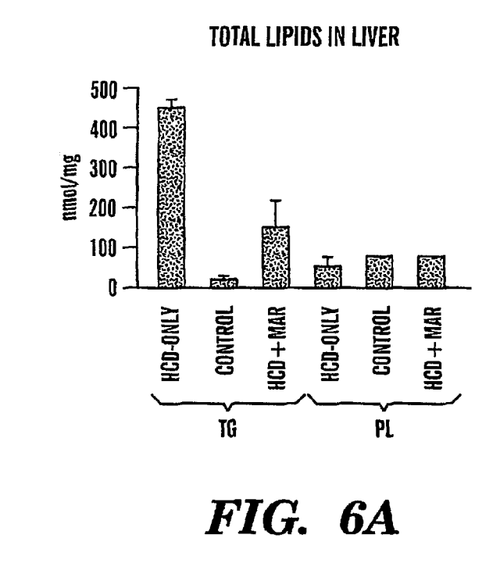
FIGS. 6A-6E show triglycerides and phospholipids in liver and serum. A. Total triglycerides and phospholipid level in liver. B. Total triglycerides and phospholipid level in serum. C. Mead/AA ratio in serum lipids. D. Levels of 16:1 in liver. E. Levels of 18:1 in liver. Total fatty acid levels in the liver go down with Marimastat™ treatment without correcting levels of monounsaturated fatty acids and mead acid in the serum, indicating that that Marimastat™ does not correct the essential fatty acid deficiency in mice on HCD.
Figure 6B:
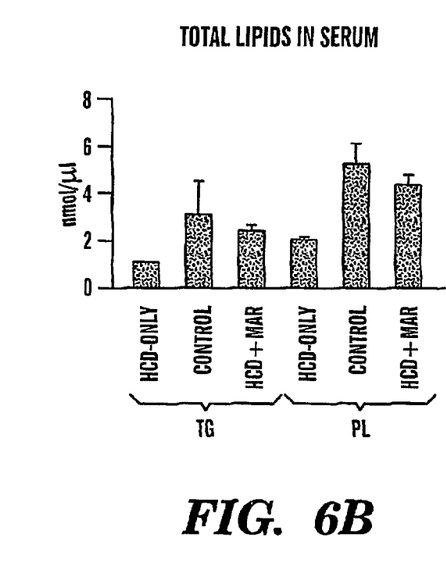
Figure 6C:
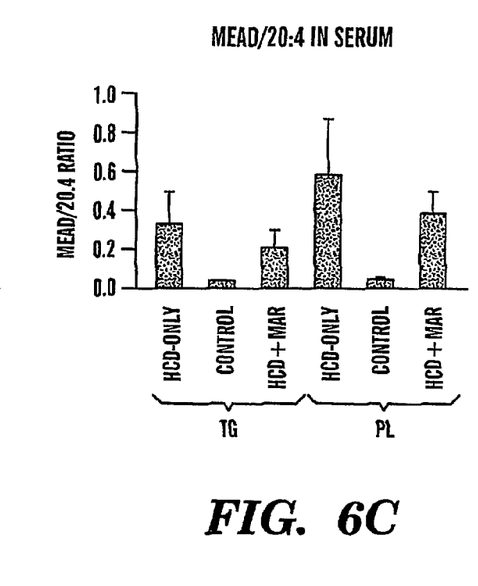

Hepatic triglyceride levels were substantially increased in HCD and significantly reduced by Marimastat™, but triglyceride levels remained higher than in controls (FIG. 6A). There were no significant differences in hepatic phospholipids among the three groups. Serum triglyceride and phospholipids were significantly reduced in HCD-only compared to control (FIG. 6B) but were normalized with Marimastat™ treatment.

Marimastat™ Does not Affect de novo Lipogenesis.

Figure 6D:
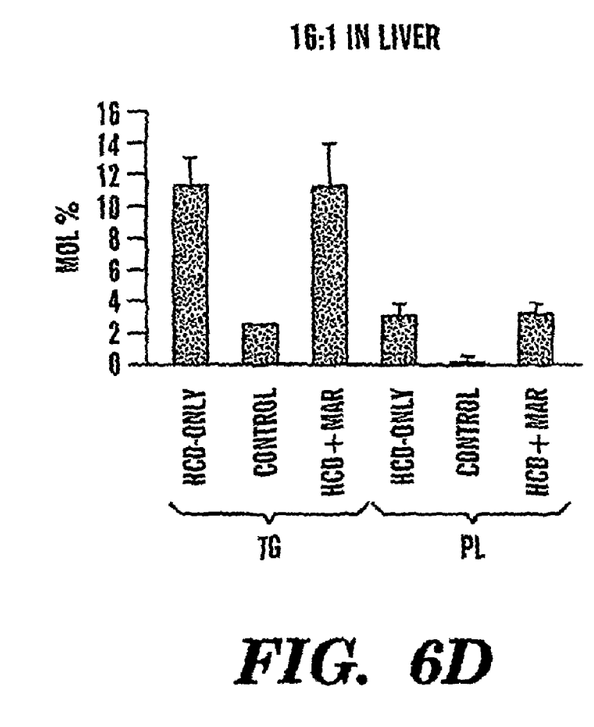
Figure 6E:
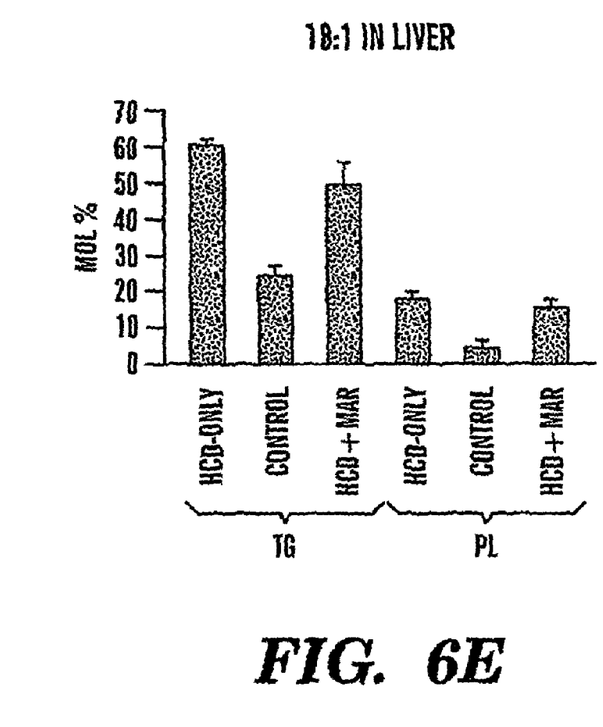

Higher levels of palmitoleic acid (16:1) and oleic acid (18:1) reflect higher levels of de novo lipogenesis. Hepatic triglyceride and phospholipid levels of 16:1 and 18:1 were substantially elevated in both HCD-only and HCD+MAR compared to control (FIGS. 6D and 6E).

The references cited herein are incorporated by reference.

REFERENCES

1. Alvarez J G, and Touchstone J C. Separation of acidic and neutral lipids by aminopropyl-bonded silica gel column chromatography. *J Chromatogr* 577: 142-145, 1992.
2. Alwayn I P, Gura K, Nose V, Zausche B, Javid P, Garza J, Verbesey J, Voss S, Ollero M, Andersson C, Bistrian B, Folkman J, and Puder M. Omega-3 fatty acid supplementation prevents hepatic steatosis in a murine model of non-alcoholic fatty liver disease. *Pediatr Res* 57: 445-452, 2005.
3. Alwayn I P, Javid P J, Gura K M, Nose V, Ollero M, and Puder M. Do polyunsaturated fatty acids ameliorate hepatic steatosis in obese mice by SREPB-1 suppression or by correcting essential fatty acid deficiency. *Hepatology* 39: 1176-1177; author reply 1177-1178, 2004.
4. Angulo P. Nonalcoholic fatty liver disease. *N Engl J Med* 346: 1221-1231, 2002.

5. Armstrong L, Godinho S I, Uppington K M, Whittington H A, and Millar A B. Contribution of TACE and Proteinase-3 to TNF-{alpha} Processing in Human Alveolar Macrophages. *Am J Respir Cell Mol Biol* 2005.
6. Bellentani S, Saccoccio G, Masutti F, Croce L S, Brandi G, Sasso F, Cristanini G, and Tiribelli C. Prevalence of and risk factors for hepatic steatosis in Northern Italy. *Ann Intern Med* 132: 112-117, 2000.
7. Benjamin D R. Hepatobiliary dysfunction in infants and children associated with long-term total parenteral nutrition. A clinico-pathologic study. *Am J Clin Pathol* 76: 276-283, 1981.
8. Brown M S, and Goldstein J L. The SREBP pathway: regulation of cholesterol metabolism by proteolysis of a membrane-bound transcription factor. *Cell* 89: 331-340, 1997.
9. Choi K C, Ryu O H, Lee K W, Kim H Y, Seo J A, Kim S G, Kim N H, Choi D S, Baik S H, and Choi K M. Effect of PPAR-alpha and -gamma agonist on the expression of visfatin, adiponectin, and TNF-alpha in visceral fat of OLETF rats. *Biochem Biophys Res Commun* 336: 747-753, 2005.
10. Clark J M, Brancati F L, and Diehl A M. Nonalcoholic fatty liver disease. *Gastroenterology* 122: 1649-1657, 2002.
11. Clark J M, Brancati F L, and Diehl A M. The prevalence and etiology of elevated aminotransferase levels in the United States. *Am J Gastroenterology* 98: 960-967, 2003.
12. Clark J M, and Diehl A M. Defining nonalcoholic fatty liver disease: implications for epidemiologic studies. *Gastroenterology* 124: 248-250, 2003.
13. Clark J M, and Diehl A M. Hepatic steatosis and type 2 diabetes mellitus. *Curr Diab Rep* 2: 210-215, 2002.
14. Cursio R, Mari B, Louis K, Rostagno P, Saint-Paul M C, Giudicelli J, Bottero V, Anglard P, Yiotakis A, Dive V, Gugenheim J, and Auberger P. Rat liver injury after normothermic ischemia is prevented by a phosphinic matrix metalloproteinase inhibitor. *Faseb J* 16: 93-95, 2002.
15. Dandona P, Aljada A, and Bandyopadhyay A. Inflammation: the link between insulin resistance, obesity and diabetes. *Trends Immunol* 25: 4-7, 2004.
16. Day C P. Pathogenesis of steatohepatitis. *Best Pract Res Clin Gastroenterol* 16: 663-678, 2002.
17. Day C P, and James O F. Steatohepatitis: a tale of two "hits"? *Gastroenterology* 114: 842-845, 1998.
18. Dekkers P E, Lauw F N, ten Hove T, te Velde A A, Lumley P, Becherer D, van Deventer S J, and van der Poll T. The effect of a metalloproteinase inhibitor (GI5402) on tumor necrosis factor-alpha (TNF-alpha) and TNF-alpha receptors during human endotoxemia. *Blood* 94: 2252-2258, 1999.
19. Deng Q G, She H, Cheng J H, French S W, Koop D R, Xiong S, and Tsukamoto H. Steatohepatitis induced by intragastric overfeeding in mice. *Hepatology* 42: 905-914, 2005.
20. Desvergne B, A I J, Devchand P R, and Wahli W. The peroxisome proliferator-activated receptors at the crossroad of diet and hormonal signalling. *J Steroid Biochem Mol Biol* 65: 65-74, 1998.
21. Feingold K R, Soued M, and Grunfeld C. Tumor necrosis factor stimulates DNA synthesis in the liver of intact rats. *Biochem Biophys Res Commun* 153: 576-582, 1988.
22. Feldstein A E, Canbay A, Angulo P, Taniai M, Burgart L J, Lindor K D, and Gores G J. Hepatocyte apoptosis and fas expression are prominent features of human nonalcoholic steatohepatitis. *Gastroenterology* 125: 437-443, 2003.
23. Feldstein A E, Canbay A, Guicciardi M E, Higuchi H, Bronk S F, and Gores G J. Diet associated hepatic steatosis sensitizes to Fas mediated liver injury in mice. *J Hepatol* 39: 978-983, 2003.
24. Fernandes J C, Martel-Pelletier J, and Pelletier J P. The role of cytokines in osteoarthritis pathophysiology. *Biorheology* 39: 237-246, 2002.
25. Glaser K B, Pease L, Li J, and Morgan D W. Enhancement of the surface expression of tumor necrosis factor alpha (TNFalpha) but not the p55 TNFalpha receptor in the THP-1 monocytic cell line by matrix metalloprotease inhibitors. *Biochem Pharmacol* 57: 291-302, 1999.
26. Haruyama T, Ajioka I, Akaike T, and Watanabe Y. Regulation and significance of hepatocyte-derived matrix metalloproteinases in liver remodeling. *Biochem Biophys Res Commun* 272: 681-686, 2000.
27. Hong F, Radaeva S, Pan H N, Tian Z, Veech R, and Gao B. Interleukin 6 alleviates hepatic steatosis and ischemia/reperfusion injury in mice with fatty liver disease. *Hepatology* 40: 933-941, 2004.
28. Horton J D, Goldstein J L, and Brown M S. SREBPs: activators of the complete program of cholesterol and fatty acid synthesis in the liver. *J Clin Invest* 109: 1125-1131, 2002.
29. Hughes C A, Talbot I C, Ducker D A, and Harran M J. Total parenteral nutrition in infancy: effect on the liver and suggested pathogenesis. *Gut* 24: 241-248, 1983.
30. Iimuro Y, Gallucci R M, Luster M I, Kono H, and Thurman R G. Antibodies to tumor necrosis factor alfa attenuate hepatic necrosis and inflammation caused by chronic exposure to ethanol in the rat. *Hepatology* 26: 1530-1537, 1997.
31. Javid P J, Greene A K, Garza J, Gura K, Alwayn I P, Voss S, Nose V, Satchi-Fainaro R, Zausche B, Mulkern R V, Jaksic T, Bistrian B, Folkman J, and Puder M. The route of lipid administration affects parenteral nutrition-induced hepatic steatosis in a mouse model. *J Pediatr Surg* 40: 1446-1453, 2005.
32. Keim N L, and Mares-Perlman J A. Development of hepatic steatosis and essential fatty acid deficiency in rats with hypercaloric, fat-free parenteral nutrition. *J Nutr* 114: 1807-1815, 1984.
33. Kersten S, Seydoux J, Peters J M, Gonzalez F J, Desvergne B, and Wahli W. Peroxisome proliferator-activated receptor alpha mediates the adaptive response to fasting. *J Clin Invest* 103: 1489-1498, 1999.
34. Kim T H, Mars W M, Stolz D B, and Michalopoulos G K. Expression and activation of pro-MMP-2 and pro-MMP-9 during rat liver regeneration. *Hepatology* 31: 75-82, 2000.
35. Knittel T, Mehde M, Grundmann A, Saile B, Scharf J G, and Ramadori G. Expression of matrix metalloproteinases and their inhibitors during hepatic tissue repair in the rat. *Histochem Cell Biol* 113: 443-453, 2000.
36. Kooby D A, Fong Y, Suriawinata A, Gonen M, Allen P J, Klimstra D S, DeMatteo R P, D'Angelica M, Blumgart L H, and Jarnagin W R. Impact of steatosis on perioperative outcome following hepatic resection. *J Gastrointest Surg* 7: 1034-1044, 2003.
37. Koteish A, and Diehl A M. Animal models of steatosis. *Semin Liver Dis* 21: 89-104, 2001.
38. Leber T M, and Balkwill F R. Regulation of monocyte MMP-9 production by TNF-alpha and a tumour-derived soluble factor (MMPSF). *Br J Cancer* 78: 724-732, 1998.
39. Li Z, Yang S, Lin H, Huang J, Watkins P A, Moser A B, Desimone C, Song X Y, and Diehl A M. Probiotics and antibodies to TNF inhibit inflammatory activity and improve nonalcoholic fatty liver disease. *Hepatology* 37: 343-350, 2003.

40. Matteoni C A, Younossi Z M, Gramlich T, Boparai N, Liu Y C, and McCullough A J. Nonalcoholic fatty liver disease: a spectrum of clinical and pathological severity. *Gastroenterology* 116: 1413-1419, 1999.
41. McMillan J I, Weeks R, West J W, Bursten S, Rice G C, and Lovett D H. Pharmacological inhibition of gelatinase B induction and tumor cell invasion. *Int J Cancer* 67: 523-531, 1996.
42. Nagase H, and Woessner J F, Jr. Matrix metalloproteinases. *J Biol Chem* 274: 21491-21494, 1999.
43. Pappo I, Bercovier H, Berry E, Gallilly R, Feigin E, and Freund H R. Antitumor necrosis factor antibodies reduce hepatic steatosis during total parenteral nutrition and bowel rest in the rat. *JPEN J Parenter Enteral Nutr* 19: 80-82, 1995.
44. Powell E E, Cooksley W G, Hanson R, Searle J, Halliday J W, and Powell L W. The natural history of nonalcoholic steatohepatitis: a follow-up study of forty-two patients for up to 21 years. *Hepatology* 11: 74-80, 1990.
45. Ratziu V, Giral P, Charlotte F, Bruckert E, Thibault V, Theodorou I, Khalil L, Turpin G, Opolon P, and Poynard T. Liver fibrosis in overweight patients. *Gastroenterology* 118: 1117-1123, 2000.
46. Roy R, Zhang B, and Moses M. Making the cut: Protease-mediated regulation of angiogenesis. *Experimental Cell Research* in press: 2005.
47. Ruan H, and Lodish H F. Insulin resistance in adipose tissue: direct and indirect effects of tumor necrosis factor-alpha. *Cytokine Growth Factor Rev* 14: 447-455, 2003.
48. Ruderman N, Chisholm D, Pi-Sunyer X, and Schneider S. The metabolically obese, normal-weight individual revisited. *Diabetes* 47: 699-713, 1998.
49. Sahoo S, and Hart J. Histopathological features of L-asparaginase-induced liver disease. *Semin Liver Dis* 23: 295-299, 2003.
50. Santucci M B, Ciaramella A, Mattei M, Sumerska T, and Fraziano M. Batimastat reduces Mycobacterium tuberculosis-induced apoptosis in macrophages. *Int Immunopharmacol* 3: 1657-1665, 2003.
51. Sax H C, and Bower R H. Hepatic complications of total parenteral nutrition. *JPEN J Parenter Enteral Nutr* 12: 615-618, 1988.
52. Sax H C, Talamini M A, Brackett K, and Fischer J E. Hepatic steatosis in total parenteral nutrition: failure of fatty infiltration to correlate with abnormal serum hepatic enzyme levels. *Surgery* 100: 697-704, 1986.
53. Sekiya M, Yahagi N, Matsuzaka T, Najima Y, Nakakuki M, Nagai R, Ishibashi S, Osuga J, Yamada N, and Shimano H. Polyunsaturated fatty acids ameliorate hepatic steatosis in obese mice by SREBP-1 suppression. *Hepatology* 38: 1529-1539, 2003.
54. Shimano H. Sterol regulatory element-binding proteins (SREBPs): transcriptional regulators of lipid synthetic genes. *Prog Lipid Res* 40: 439-452, 2001.
55. Shimano H, Horton J D, Shimomura I, Hammer R E, Brown M S, and Goldstein J L. Isoform 1c of sterol regulatory element binding protein is less active than isoform 1a in livers of transgenic mice and in cultured cells. *J Clin Invest* 99: 846-854, 1997.
56. Sun Z, Klein A S, Radaeva S, Hong F, El-Assal O, Pan H N, Jaruga B, Batkai S, Hoshino S, Tian Z, Kunos G, Diehl A M, and Gao B. In vitro interleukin-6 treatment prevents mortality associated with fatty liver transplants in rats. *Gastroenterology* 125: 202-215, 2003.
57. Teli M R, James O F, Burt A D, Bennett M K, and Day C P. The natural history of nonalcoholic fatty liver: a follow-up study. *Hepatology* 22: 1714-1719, 1995.
58. Tilg H, and Diehl A M. Cytokines in alcoholic and nonalcoholic steatohepatitis. *N Engl J Med* 343: 1467-1476, 2000.
59. Wanless I R, and Lentz J S. Fatty liver hepatitis (steatohepatitis) and obesity: an autopsy study with analysis of risk factors. *Hepatology* 12: 1106-1110, 1990.
60. Watanabe Y, Haruyama T, and Akaike T. Liver-derived matrix metalloproteinase-9 (gelatinase B) recruits progenitor cells from bone marrow into the blood circulation. *Biol Pharm Bull* 26: 564-568, 2003.
61. Werner A, Having a R, Bos T, Bloks V W, Kuipers F, and Verkade H J. Essential fatty acid deficiency in mice is associated with hepatic steatosis and secretion of large VLDL particles. *Am J Physiol Gastrointest Liver Physiol* 288: G1150-1158, 2005.
62. Whalen G F, Shamberger R C, Perez-Atayde A, and Folkman J. A proposed cause for the hepatic dysfunction associated with parenteral nutrition. *J Pediatr Surg* 25: 622-626, 1990.
63. Wielockx B, Lannoy K, Shapiro S D, Itoh T, Itohara S, Vandekerckhove J, and Libert C. Inhibition of matrix metalloproteinases blocks lethal hepatitis and apoptosis induced by tumor necrosis factor and allows safe antitumor therapy. *Nat Med* 7: 1202-1208, 2001.
64. Xu J, Storer P D, Chavis J A, Racke M K, and Drew P D. Agonists for the peroxisome proliferator-activated receptor-alpha and the retinoid X receptor inhibit inflammatory responses of microglia. *J Neurosci Res* 81: 403-411, 2005.
65. Yahagi N, Shimano H, Hasty A H, Matsuzaka T, Ide T, Yoshikawa T, Amemiya-Kudo M, Tomita S, Okazaki H, Tamura Y, Iizuka Y, Ohashi K, Osuga J, Harada K, Gotoda T, Nagai R, Ishibashi S, and Yamada N. Absence of sterol regulatory element-binding protein-1 (SREBP-1) ameliorates fatty livers but not obesity or insulin resistance in Lep(ob)/Lep(ob) mice. *J Biol Chem* 277: 19353-19357, 2002.

What is claimed is:

1. A method for treating a fatty liver disease or disorder in a patient in need thereof, comprising selecting a patient in need of treatment and administering Marimastat to said patient.

2. The method of claim 1, wherein the fatty liver disease or disorder is NAFLD, NASH, ALD, fatty liver associated with chronic hepatitis infection, TPN, gastrointestinal operations, diabetes and Reye's Syndrome.

3. The method of claim 1, wherein the fatty liver disease is associated with TPN and the patient is an infant.

4. The method of claim 1, wherein the patient is obese.

* * * * *